United States Patent [19]

Miyano et al.

[11] 4,404,378
[45] Sep. 13, 1983

[54] 2-SUBSTITUTED OR UNSUBSTITUTED AMINOCARBONYLOXYALKYL-1,4-DIHYDROPYRIDINES

[75] Inventors: Tetsuji Miyano; Kunio Suzuki, both of Nagoya; Nobuo Harada, Okazaki, all of Japan

[73] Assignee: Banyu Pharmaceutical Co., Ltd., Tokyo, Japan

[21] Appl. No.: 366,137

[22] Filed: Apr. 6, 1982

[30] Foreign Application Priority Data

Apr. 23, 1981 [JP] Japan .................... 56-60677

[51] Int. Cl.³ .................. C07D 413/12; C07D 211/90
[52] U.S. Cl. ..................... 544/131; 544/357; 544/365; 546/194; 546/263; 546/281; 546/321
[58] Field of Search ............... 546/321, 194, 263, 281; 544/131, 357, 365

[56] References Cited

FOREIGN PATENT DOCUMENTS 2629892 1/1977 Fed. Rep. of Germany.
2658183 7/1978 Fed. Rep. of Germany.
2844595 9/1980 Fed. Rep. of Germany.

Primary Examiner—Henry R. Jiles
Assistant Examiner—Bernard Dentz
Attorney, Agent, or Firm—Oblon, Fisher, Spivak, McClelland & Maier

[57] ABSTRACT

Novel compounds having vasodilation and hypotensive effects are represented by the formula

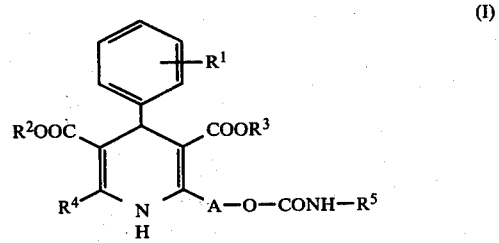

(I)

where $R^1$ is halogen, nitro, cyano or lower alkoxy; each of $R^2$ and $R^3$ is lower alkyl, lower haloalkyl, lower alkoxyalkyl, aralkyloxyalkyl, aryloxyalkyl, lower alkenoxyalkyl, N,N-di-lower alkylaminoalkyl, N-lower alkyl-N-aralkylaminoalkyl, piperidylalkyl, 4-lower alkyl piperazinylalkyl, norpholinoalkyl or 1-pyrrolidinylalkyl; $R^4$ is lower alkyl; A is lower alkylene; and $R^5$ is hydrogen, lower alkyl, cycloalkyl of 3 to 7 carbon atoms, or aryl unsubstituted or substituted by one or two substituents selected from halogen, nitro, lower alkyl, lower alkoxy, di-lower alkylamino and cyano.

Also disclosed are processes for their preparation.

9 Claims, No Drawings

2-SUBSTITUTED OR UNSUBSTITUTED AMINOCARBONYLOXYALKYL-1,4-DIHYDROPYRIDINES

BACKGROUND OF THE INVENTION

1. Field of the Invention

The present invention relates to novel 2-substituted or unsubstituted aminocarbonyloxyalkyl-1,4-dihydropyridines and processes for their preparation. The novel compounds of the present invention have vasodilation activities and hypotensive activities and thus they are useful for the treatment of cardiac peripheral disorders, intracerebral vascular disorders or hypertension.

2. Description of the Prior Art

It has been known that nifedipine represented by the following formula has coronary vasodilation activities or hypotensive activities (U.S. Pat. No. 3,485,847 to Friedrich Bossert et al):

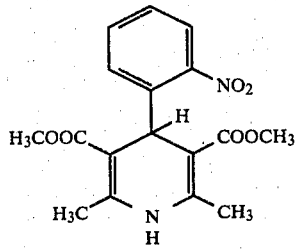

However, 2-substituted or unsubstituted aminocarbonyloxyalkyl-1,4-dihydropyridines have not been known.

SUMMARY OF THE INVENTION

It is an object of the present invention to provide novel 2-substituted or unsubstituted aminocarbonyloxyalkyl-1,4-dihydropyridines which have greater vasodilation activities and substantially less toxicity than the conventional 1,4-dihydropyridines and thus are quite useful as medicines.

Another object of the present invention is to provide processes for the preparation of the novel compounds.

Thus, the present invention provides a novel 2-substituted or unsubstituted aminocarbonyloxyalkyl-1,4-dihydropyridine represented by the general formula

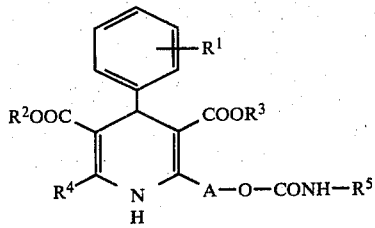

(I)

where $R^1$ is halogen, nitro, cyano or lower alkoxy; each of $R^2$ and $R^3$ is lower alkyl, lower haloalkyl, lower alkoxyalkyl, aralkyloxyalkyl, aryloxyalkyl, lower alkenoxyalkyl, N,N-di-lower alkylaminoalkyl, N-lower alkyl-N-aralkylaminoalkyl, piperidylalkyl, 4-lower alkyl piperazinylalkyl, morpholinoalkyl, or 1-pyrrolidinylalkyl; $R^4$ is lower alkyl; A is lower alkylene; and $R^5$ is hydrogen, lower alkyl, cycloalkyl of 3 to 7 carbon atoms, or aryl unsubstituted or substituted by one or two substituents selected from halogen, nitro, lower alkyl, lower alkoxy, di-lower alkylamino and cyano.

The compounds of the general formula I according to the present invention can be prepared by the following two processes.

According to the first process, the compounds of the general formula I are prepared by reacting a 2-hydroxyalkyl-1,4-dihydropyridine represented by the general formula

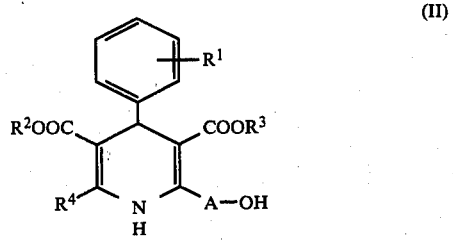

(II)

where $R^1$, $R^2$, $R^3$, $R^4$ and A re as defined above, with an isocyanate represented by the general formula $R^6NCO$ where $R^6$ is chlorosulfonyl, dichlorophosphoryl, lower alkyl, cycloalkyl of 3 to 7 carbon atoms, or aryl unsubstituted or substituted by one or two substituents selected from halogen, nitro, lower alkyl, lower alkoxy, di-lower alkylamino and cyano, or a compound capable of forming said isocyanate under the reaction condition, and, if necessary, hydrolyzing the reaction product.

According to the second process of the invention, a 3- and/or 5-aminoalkoxycarbonyl-2-substituted or unsubstituted aminocarbonyloxyalkyl-1,4-dihydropyridine represented by the general formula

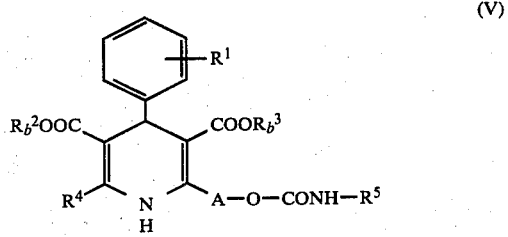

(V)

where $R^1$, $R^4$, A and $R^5$ are as defined above, and one of $R_b^2$ and $R_b^3$ is N,N-di-lower alkylaminoalkyl, N-lower alkyl-N-aralkylaminoalkyl, piperidylalkyl, 4-lower alkyl piperazinylalkyl, morpholinoalkyl or 1-pyrrolidinylalkyl and the other is lower alkyl, lower alkoxyalkyl, aralkyloxyalkyl, aryloxyalkyl, lower alkenoxyalkyl, N,N-di-lower alkylaminoalkyl, N-lower alkyl-N-aralkylaminoalkyl, piperidyl alkyl, 4-lower alkyl piperazinylalkyl, morpholinoalkyl or 1-pyrrolidinylalkyl, is prepared by reacting a 3- and/or 5-haloalkoxycarbonyl-2-substituted or unsubstituted aminocarbonyloxyalkyl-1,4-dihydropyridine represented by the general formula

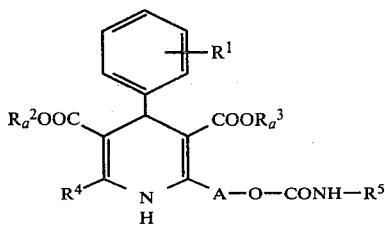

(III)

where $R^1$, $R^4$, A and $R^5$ are as defined above, and one of $R_a^2$ and $R_a^3$ is lower haloalkyl and the other is lower alkyl, lower haloalkyl, lower alkoxyalkyl, aralkyloxyalkyl, aryloxyalkyl or lower alkenoxyalkyl, with an amine represented by the general formula

(IV)

where each of $R^6$ and $R^7$ is lower alkyl, aralkyl or aryl, or $R^6$ and $R^7$ may form together with the nitrogen atom a heterocyclic group.

DETAILED DESCRIPTION OF THE PREFERRED EMBODIMENTS

Referring to the above general formula I, specific examples of $R^1$ to $R^5$ and A are as follows:

$R^1$ is halogen such as chlorine, bromine or iodine; nitro; cyano; or lower alkoxy such as methoxy, ethoxy, propoxy or butoxy.

Each of $R^2$ and $R^3$ is lower alkyl such as methyl, ethyl, propyl, isopropyl, butyl, isobutyl, tert.-butyl, pentyl or hexyl; lower haloalkyl such as β-chloroethyl, β-bromoethyl, β-chloropropyl, γ-chloropropyl, β,β-dichloroethyl or β,β,β-trichloroethyl; lower alkoxyalkyl such as β-methoxyethyl, β-ethoxyethyl, β-propoxyethyl, β-isopropoxyethyl, β-butoxyethyl, β-isobutoxyethyl, β-tert.-butoxyethyl, β-methoxypropyl, β-ethoxypropyl, β-propoxypropyl, γ-methoxypropyl, γ-ethoxypropyl or γ-propoxypropyl; aralkyloxyalkyl such as β-benzyloxyethyl, β-phenethyloxyethyl, or β-(p-bromobenzyloxy)ethyl; aryloxyalkyl such as β-phenoxyethyl, β-(p-chlorophenoxy)ethyl or β-tolyloxyethyl; lower alkenoxyalkyl such as β-vinyloxyethyl, β-allyloxyethyl or β-(3-butenyloxy)ethyl; N,N-di-lower alkylaminoalkyl such as β-dimethylaminoethyl, β-diethylaminoethyl or β-ethylmethylaminoethyl; N-lower alkyl N-aralkylaminoethyl such as β-benzylmethylaminoethyl, β-benzylethylaminoethyl, β-(p-bromobenzylmethylamino)ethyl or β-(α-methylbenzylmethylamino)ethyl; piperidylalkyl such as β-piperidylethyl or β-piperidylpropyl; 4-lower alkyl piperazinylalkyl such as β-(4-methylpiperazinyl)ethyl, β-(4-ethylpiperazinyl)ethyl or β-(4-methylpiperazinyl)propyl; morpholinoalkyl such as β-morpholinoethyl, β-morpholinopropyl or γ-morpholinopropyl; or 1-pyrrolidinylalkyl.

$R^4$ is lower alkyl such as methyl, ethyl, propyl or isopropyl.

A is ethylene or propylene which may be unsubstituted or substituted by methyl, ethyl or isopropyl.

$R^5$ is hydrogen; lower alkyl such as methyl, ethyl, propyl, isopropyl, butyl, isobutyl, tert.-butyl, pentyl or hexyl; cycloalkyl such as cyclopropyl, cyclobutyl, cyclopentyl, cyclohexyl or cycloheptyl; aryl such as phenyl, p-chlorophenyl, p-bromophenyl, p-fluorophenyl, m,p-dichlorophenyl, p-nitrophenyl, p-tolyl, p-methoxyphenyl, p-dimethylaminophenyl, p-cyanophenyl, α-pyridyl, β-pyridyl or γ-pyridyl.

Now, the processes for preparing the compounds of the general formula I according to the present invention will be described in detail.

The first process is concerned with the preparation of the 2-aminocarbonyloxyalkyl-1,4-dihydropyridines represented by the general formula I by reacting a hydroxyalkyl compound represented by the above general formula II with an isocyanate represented by $R^6$NCO where $R^6$ is as defined above.

The starting compounds of the general formula II are known compounds or may readily be prepared by known methods if not disclosed in literatures. For instance, 2-hydroxymethyl-6-methyl-4-(3-nitrophenyl)-3-ethoxycarbonyl-5-(β-ethoxyethoxy)carbonyl-1,4-dihydropyridine can be prepared by the method disclosed in Japanese Laid-Open Patent Application No. 5777/77.

As the isocyanate represented by the general formula $R^6$NCO where $R^6$ is as defined above, there may be mentioned chlorosulfonyl isocyanate, dichlorophosphoryl isocyanate, methyl isocyanate, ethyl isocyanate, propyl isocyanate, isopropyl isocyanate, butyl isocyanate, isobutyl isocyanate, tert.-butyl isocyanate, allyl isocyanate, cyclohexyl isocyanate, cyclopentyl isocyanate, phenyl isocyanate, o-, m- or p-chlorophenyl isocyanate, o-, m- or p-nitrophenyl isocyanate, m,p-dichlorophenyl isocyanate, p-fluorophenyl isocyanate, p-methoxyphenyl isocyanate, p-tolyl isocyanate, p-dimethylaminophenyl isocyanate, benzyl isocyanate, diphenylmethyl isocyanate, phenethyl isocyanate or β-dimethylaminoethyl isocyanate.

Instead of the isocyanate represented by the formula $R^6$NCO where $R^6$ is as defined above, a compound capable of forming such an isocyanate under the reaction condition may be used for the reaction of the first process. As such a compound, there may be mentioned an acid azide represented by the general formula $R^5$CON where $R^5$ is as defined above, under heating, or a thiolcarbamate represented by the general formula $R^5$NHCOSR where $R^5$ is as defined above and R is lower alkyl, under heating or in the presence of trialkylamine and heavy metal (for instance, silver nitrate or mercury chloride).

In the first process, the reaction conditions for the preparation of the compounds of the formula I are suitable selected depending upon the natures of the particular reactants employed. Usually, however, the isocyanate of the formula $R^6$NCO where $R^6$ is as defined above, is used in an amount of from 1 to 5 moles, preferably from 1 to 2 moles relative to 1 mole of the 1,4-dihydropyridine derivative of the formula II. The reaction is usually carried out under cooling, at room temperature or under heating. As the reaction solvent, there may be used benzene, toluene, chloroform, dichloromethane, chlorobenzene, dioxane, tetrahydrofuran, diethyl ether, acetonitrile, pyridine, dimethylformamide, ethylacetate, or acetone. The reaction can advantageously carried out in the presence of a catalyst. As the catalyst, there may be used a tertiary amine such as triethylamine, trimethylamine, N-alkylpiperidine, N-alkylmorpholine, N,N-dialkylaniline or pyridine, or sodium hydroxide, sodium carbonate or sodium hydrogen carbonate. In a case where chlorosulfonyl isocyanate or dichlorophosphoryl isocyanate is used as the isocyanate, it is necessary to carry out hydrolysis treatment of the reaction product with an addition of water to the reaction mixture after the completion of the reaction.

The second process is concerned with the preparation of 2-aminocarbonyloxyalkyl-3- and/or 5-aminoalkoxycarbonyl-1,4-dihydropyridines of the general formula V by reacting a 2-aminocarbonyloxyalkyl-3- and/or 5-haloalkoxycarbonyl-1,4-dihydropyridine of the general formula III with an amine of the general formula IV.

The starting compounds of the formula III may be prepared by the first process.

As the amine of the general formula IV, there may be used dimethylamine, diethylamine, methylethylamine, N-methylaniline, N-methylbenzylamine or N-methyl-p-chlorobenzylamine.

As the reaction solvent for the second process, there may be used methanol, ethanol, propanol, isopropanol, dimethylformamide or tetrahydrofuran. This reaction can advantageously carried out in the presence of e.g. lithium iodide or sodium iodide. The reaction is carried out at room temperature or under heating for from 2 to 20 hours.

The compounds I prepared by the processes of the present invention may be refined, isolated or collected by usual methods such as extraction treatment with use of an organic solvent, chromatography with use of silica gel or alumina, or crystallization. Further, in a case where the compounds thus prepared are capable of forming a salt, they may be converted to the respective salts with use of an inorganic acid such as hydrochloric acid or an organic acid.

The compounds of the general formula I of the present invention have vasodilation activities and hypotensive activities. Particularly, they have strong coronary vasodilation activities and extremely weak toxicity, and thus, they are expected to be quite useful as drugs for the treatment of diseases of the circulation system such as hypertension, cardiac insufficiency, angina pectoris, myocardial infarction or intracerebral vascular disorders.

PHARMACOLOGY

Pharmacological and toxicity tests have been conducted with respect to various compounds representing the 2-substituted or unsubstituted aminocarbonyloxyalkyl-1,4-dihydropyridines of the present invention.

1. Test methods (a) Coronary vasodilation

According to Langendorff method (O. Langendorff; Pflügers arch. ges. phisiol., 61, 291–332 (1895)), the coronary vasodilation effects were tested using isolated hearts of rabbits. The strength of coronary vasodilation was evaluated by $ICD_{50}(g/ml)$ i.e. the dosage of a sample required to increase the coronary outflow by 50%.

(b) Acute toxicity

Samples were intravenously administered to DM strain male mice (18 to 22 g), and $LD_{50}$ values were obtained according to the up-and-down method.

(c) Coronary effects on dogs

Beagle dogs (13 to 16 kg. ♂) were subjected to thoracotomy under anesthesia with sodium pentobarbital, and a probe was attached to the heart left coronary anterior descending artery of each animal, whereupon the coronary blood flow (CF) was measured by an electromagnetic flowmeter. On the other hand, a probe was attached to the exposed right femoral artery, and the femoral artery blood flow (FAF) was measured by an electromagnetic flowmeter. A canule was inserted to the left femoral artery, and the systemic blood pressure (BP) was bloody measured by a transducer.

The heart rate (HR) was measured by an electrocardiogram.

The sample solution was intravenously injected to the right femoral vein.

The coronary blood flow (CF), the femoral artery blood flow (FAF) and the heart rate (HR) were represented by a % increase upon the injection of each sample as compared with the respective control value upon the injection of a saline.

The systemic blood pressure (BP) was represented by a % increase as compared with the control.

2. Results

The coronary vasodilation effects on the isolated heart preparations of rabbits and acute toxicity against the mice are shown in Tables 1(a) and 1(b). It is seen that the compounds of the present invention exhibit strong coronary vasodilation effects against the coronary vessels. The acute toxicity thereof is as low as 1/6 to 1/17 of the acute toxicity of nifedipine.

The coronary effects against the beagle dogs are shown in Table 2. It is seen that the five representative compounds of the present invention increase the coronary blood flow (CF) in correspondence with the increase of their doses, and their effectiveness is equivalent to or greater than the nifedipine. It is also seen that the coronary effects are thereby obtainable without substantially decreasing the systemic blood pressure (BP) or without substantially affecting the heart rate (HR). Thus, no excessive load will be given to the heart, which, couples with the minimized toxicity, makes the compounds of the present invention quite useful coronary vasodilators.

Further, from the results of a separate pharmacological test where 1 to 10 μg/kg of the compounds of Examples 3, 26 and 38 were intravenously administered, it was found that they increased the cerebral blood flow and the peripheral blood flow by from 40 to 50%, thus indicating that the compounds of the present invention are useful also as cerebral vasodilators and peripheral vasodilators.

TABLE 1(a)

| | Coronary vasodilation and acute toxicity | |
|---|---|---|
| No. Compounds: | Coronary vasodilation $ICD_{50}$ g/ml | Acute toxicity $LD_{50}$ mg/kg, i.v. |
| Reference compound: | | |
| 2,6-Dimethyl-4-(2-nitrophenyl)-3,5-dimethoxycarbonyl-1,4-dihydropyridine (nifedipine) | $2.9 \times 10^{-7}$ | 11.5 |
| Compounds of the present invention: | | |

TABLE 1(a)-continued

Coronary vasodilation and acute toxicity

| No. | Compounds: | Coronary vosodilation $ICD_{50}$ g/ml | Acute toxicity $LD_{50}$ mg/kg, i.v. |
|---|---|---|---|
| (1) | 2-Aminocarbonyloxymethyl-6-methyl-4-(3-nitrophenyl)-3,5-diethoxycarbonyl-1,4-dihydropyridine | $2.4 \times 10^{-7}$ | 207 |
| (2) | 2-N—Methylaminocarbonyloxymethyl-6-methyl-4-(3-nitrophenyl)-3,5-diethoxycarbonyl-1,4-dihydropyridine | $3.2 \times 10^{-7}$ | 71 |
| (3) | 2-Aminocarbonyloxymethyl-6-methyl-4-(3-nitrophenyl)-3,5-dimethoxycarbonyl-1,4-dihydropyridine | $3.6 \times 10^{-7}$ | 167 |
| (4) | 2-N—Methylaminocarbonyloxymethyl-6-methyl-4-(3-nitrophenyl)-3,5-dimethoxycarbonyl-1,4-dihydropyridine | $3.6 \times 10^{-7}$ | 84 |
| (5) | 2-Aminocarbonyloxymethyl-6-methyl-4-(2-nitrophenyl)-3,5-diethoxycarbonyl-1,4-dihydropyridine | $4.8 \times 10^{-7}$ | 104 |
| (6) | 2-N—Methylaminocarbonyloxymethyl-6-methyl-4-(2-nitrophenyl)-3,5-diethoxycarbonyl-1,4-dihydropyridine | $4.5 \times 10^{-7}$ | 30 |
| (7) | 2-Aminocarbonyloxymethyl-6-methyl-4-(3-nitrophenyl)-3-ethoxycarbonyl-5-isopropoxycarbonyl-1,4-dihydropyridine | $2.4 \times 10^{-7}$ | 76 |
| (8) | 2-N—Methylaminocarbonyloxymethyl-6-methyl-4-(3-nitrophenyl)-3-ethoxycarbonyl-5-isopropoxycarbonyl-1,4-dihydropyridine | $2.3 \times 10^{-7}$ | 37 |

TABLE 1(b)

Coronary vasodilation and acute toxicity

| No | Compounds: | Coronary vasodilation $ICD_{50}$ g/ml | Acute toxicity $LD_{50}$ mg/kg, i.v. |
|---|---|---|---|
| | Reference compound; | | |
| | 2,6-Dimethyl-4-(2-nitrophenyl)-3,5-dimethoxycarbonyl-1,4-dihydropyridine (nifedipine) | $2.2 \times 10^{-7}$ | 11.5 |
| | Compounds of the present invention: | | |
| (9) | 2-Aminocarbonyloxymethyl-6-methyl-4-(3-nitrophenyl)-3-ethoxycarbonyl-5-(β-propoxyethoxy)carbonyl-1,4-dihydropyridine | $3.4 \times 10^{-7}$ | 136 |
| (10) | 2-Aminocarbonyloxymethyl-6-methyl-4-(2-nitrophenyl)-3-ethoxycarbonyl-5-(β-propoxyethoxy)carbonyl-1,4-dihydropyridine | $3.0 \times 10^{-7}$ | 84 |
| (11) | 2-Aminocarbonyloxymethyl-6-methyl-4-(3-nitrophenyl)-5-ethoxycarbonyl-3-(β-propoxyethoxy)carbonyl-1,4-dihydropyridine | $2.5 \times 10^{-7}$ | 123 |
| (12) | 2-Aminocarbonyloxymethyl-6-methyl-4-(3-nitrophenyl)-3,5-bis[(β-propoxyethoxy)carbonyl]-1,4-dihydropyridine | $1.5 \times 10^{-7}$ | 123 |
| (13) | 2-N—Methylaminocarbonyloxymethyl-6-methyl-4-(3-nitrophenyl)-3,5-bis[(β-propoxyethoxy)carbonyl]-1,4-dihydropyridine | $4.0 \times 10^{-8}$ | 104 |
| (14) | 2-N—Cyclohexylaminocarbonyloxymethyl-6-methyl-5-ethoxycarbonyl-3-(β-methoxyethoxy)carbonyl-1,4-dihydropyridine | $3.5 \times 10^{-7}$ | 88 |
| (15) | 2-Aminocarbonyloxymethyl-6-methyl-4-(3-nitrophenyl)-3-methoxycarbonyl-5-(β-N—methylbenzylaminoethoxy)carbonyl-1,4-dihydropyridine | $4.0 \times 10^{-7}$ | >200 |
| (16) | 2-N—Methylaminocarbonyloxymethyl-6-methyl-4-(3-nitrophenyl)-3-methoxycarbonyl-5-(β-N—methylbenzylaminoethoxy)carbonyl-1,4-dihydropyridine | $2.5 \times 10^{-7}$ | 146 |
| (17) | 2-Aminocarbonyloxymethyl-6-methyl-4-(3-nitrophenyl)-3-methoxycarbonyl-5-[β-(4-methyl-1-piperazinyl)ethoxycarbonyl]-1,4-dihydropyridine | $2.0 \times 10^{-6}$ | 68 |
| (18) | 2-Aminocarbonyloxymethyl-6-methyl-4-(3-nitrophenyl)-3-methoxycarbonyl-5-(β-morpholinoethoxy)carbonyl-1,4-dihydropyridine | $1.5 \times 10^{-6}$ | >200 |
| (19) | 2-Aminocarbonyloxymethyl-6-methyl-4-(3-nitrophenyl)-3-(β-propoxyethoxy)carbonyl-5-(β-N—methylbenzylaminoethoxy)carbonyl-1,4-dihydropyridine | $1.8 \times 10^{-7}$ | 168 |
| (20) | 2-Aminocarbonyloxymethyl-6-methyl-4-(2-chlorophenyl)-3,5-bis[(β-methoxyethoxy)carbonyl]-1,4-dihydropyridine | $3.6 \times 10^{-7}$ | 184 |
| (21) | 2-(4-chlorophenyl)aminocarbonyloxymethyl-6-methyl-4-(3-nitrophenyl)-3-ethoxycarbonyl-5-isopropoxycarbonyl-1,4-dihydropyridine | $2.8 \times 10^{-7}$ | 83 |
| (22) | 2-N—Phenylaminocarbonyloxymethyl-6-methyl-4-(3-nitrophenyl)-3-ethoxycarbonyl-5-isopropoxycarbonyl-1,4-dihydropyridine | $3.3 \times 10^{-7}$ | 80 |

TABLE 2

| No. | Compound | Dose μg/kg i.v. | CF % increase | FAF % increase | BP % decrease | HR % increase |
|---|---|---|---|---|---|---|
| | Nifedipine | 1 | 10 | −3 | 2 | 0.6 |
| | | 3 | 48 | −4 | 10 | 2 |
| | | 10 | 86 | 10 | 18 | 4 |
| (1) | [structure: 3-NO2-phenyl dihydropyridine with C2H5OOC, COOC2H5, CH3, CH2O—CONH2] | 1 | 4 | 7 | 0 | 0 |
| | | 3 | 30 | 10 | 2 | 2 |
| | | 10 | 74 | 24 | 10 | 4 |
| (2) | [structure: 3-NO2-phenyl dihydropyridine with n-C3H7OCH2CH2OOC, COOCH2CH2O—n-C3H7, CH3, CH2O—CONH2] | 1 | 14 | 13 | 3 | 0 |
| | | 3 | 50 | 25 | 4 | 0 |
| | | 10 | 90 | 65 | 15 | −2 |
| (3) | [structure: 3-NO2-phenyl dihydropyridine with n-C3H7OCH2CH2OOC, COOCH2CH2O—n-C3H7, CH3, CH2O—CONH—CH3] | 1 | 12 | 2 | 2 | 0 |
| | | 3 | 51 | 10 | 2 | 0 |
| | | 10 | 95 | 25 | 20 | −5 |
| (4) | [structure: 3-NO2-phenyl dihydropyridine with C6H5—CH2, CH3—NCH2CH2OOC, COOCH2CH2O—n-C3H7, CH3, CH2O—CONH2] | 1 | 13 | 13 | 0 | 0 |
| | | 3 | 45 | 17 | 4 | 0 |
| | | 10 | 88 | 27 | 15 | −3 |
| (5) | [structure: 3-NO2-phenyl dihydropyridine with i-C3H7OOC, COOC2H5, CH3, CH2O—CONH—(4-Cl-phenyl)] | 1 | 13 | 8 | 0 | 0 |
| | | 3 | 38 | 35 | 2 | 0 |
| | | 10 | 86 | 82 | 22 | −10 |

PREPARATION OF STARTING COMPOUNDS

Reference Example 1 m-Nitrobenzaldehyde (4.5 g), β-ethoxyethyl acetoacetate (5.5 g) and piperidine (0.4 ml) were dissolved in benzene (30 ml), and refluxed under heating for 4 hours under an azeotropic dehydration condition. After cooling the reaction mixture, it was washed with water, dried and subjected to concentration under reduced pressure to distill off the solvent. The oily residue and ethyl 4,4-dimethoxy-3-aminocrotonate (5.7 g) were dissolved in ethanol (30 ml), and reacted under stirring at 90° C. for 8 hours. After cooling the reaction mixture, the solvent was distilled off by distillation under reduced pressure, and the residue was extracted with ethyl acetate. The extracted solution was washed with water and dried, and subjected to concentration under reduced pressure to distill off the solvent. The oily residue was subjected to separation and purification by means of silica gel column chromatography with use of a developer solvent (hexane:ethyl acetate=8:5), whereupon 4-(3-nitrophenyl-2-dimethoxymethyl-6-methyl-3-ethoxycarbonyl-5-(β-ethoxyethoxy)carbonyl-1,4-dihydropyridine (8.95 g) was obtained as a yellow oily substance.

This yellow oily substance was dissolved in acetone (100 ml), 6 N hydrochloric acid (20 ml) was added, and the mixture was reacted under stirring at room temperature for 5 hours. The reaction mixture was neutralized with sodium hydrogen carbonate to pH 7, the acetone was distilled off by concentration under reduced pressure and the residue was extracted with ethyl acetate. The extracted solution was washed with water, dried and then subjected to concentration under reduced pressure to distill off the solvent. The residue (an aldehyde compound) was dissolved in ethanol (200 ml), sodium boron hydride (860 mg) was added under cooling, and the mixture was reacted under stirring for one hour. The reaction mixture was adjusted to pH 4 (with 1 N hydrochloric acid) and concentrated under reduced pressure. The residue was extracted with ethyl acetate, and the extracted solution was washed with water, dried and subjected to concentration under reduced pressure to distill off the solvent. The residue was purified by silica gel column chromatography with use of a developer solvent (hexane:ethyl acetate=1:1), whereupon 4-(3-nitrophenyl)-2-hydroxymethyl-6-methyl-3-ethoxycarbonyl-5-(β-ethoxyethoxy)carbonyl-1,4-dihydropyridine (4.2 g) was obtained in a crystal form.

UV (in MeOH): λmax=236, 356 nm.

NMR (90 MHz, CDCl₃): δ1.05–1.4 (m, 6H), 2.4 (s, 3H), 3.08 (br. s. 1H), 3.55 (q, J=7 Hz, 2H), 3.65 (t, J=4 Hz, 2H), 4.12 (q, J=8 Hz, 2H), 4.22 (t, J=4 Hz, 2H), 4.84 (s, 2H), 5.18 (s, 1H), 7.35–8.3 (m, 5H)

Reference Example 2 m-Nitrobenzaldehyde (4.5 g), β-chloroethyl acetoacetate (5 g), piperidine (0.2 ml) and glacial acetic acid (0.2 ml) were dissolved in benzene (30 ml) and refluxed under heating for 4 hours under an azeotropic dehydration condition. The reaction mixture was washed with water, dried and subjected to concentration under reduced pressure to distill off the solvent. The residue and methyl 4,4-dimethoxy-3-aminocrotonate (5.5 g) thereby obtained, were dissolved in propanol (50 ml) and reacted under stirring at 90° C. for 8 hours. The solvent was distilled off from the reaction mixture, and the reaction mixture was mixed with acetone (50 ml). After removing the insoluble matters by filtration, 6 N hydrochloric acid (10 ml) was added to the filtrate, and the mixture was reacted under stirring at room temperature for 4 hours. The reaction mixture was neutralized with sodium hydrogen carbonate, and then the solvent was distilled off. The residue was extracted with ethyl acetate, and the extracted solution was washed with water and dried, and the solvent was distilled off. The oily residue was dissolved in ethanol (50 ml), sodium boron hydride (1.3 g) was added under cooling, and the mixture was reacted under stirring for 2 hours. The reaction mixture was adjusted to pH 4 and concentrated. The residue was extracted with ethyl acetate. The extracted solution was washed with water, again dried and concentrated. The residue was separated and purified by silica gel column chromatography with use of a developer solvent (hexane:ethyl acetate=1:1), whereupon 4-(3-nitrophenyl)-2-hydroxymethyl-6-methyl-3-methoxycarbonyl-5-(β-chloroethoxy)carbonyl-1,4-dihydropyridine (6.8 g) was obtained in a crystal form.

IR (KBr): 3380, 2940, 1670, 1530, 1470, 1350, 1210, 1100, 900, 780, 740, 705 cm⁻¹.

NMR (90 MHz, DMSO-d₆): δ2.45 (s, 3H), 2.75 (br, s, 1H), 3.52 (s, 3H), 3.7 (t, J=6 Hz, 2H), 4.38 (t, J=6 Hz, 2H), 4.86 (s, 2H), 5.18 (s, 1H), 7.4–8.3 (m, 5H).

EXAMPLE 1

2-Aminocarbonyloxymethyl-6-methyl-4-(2-nitrophenyl)-3,5-diethoxycarbonyl-1,4-dihydropyridine

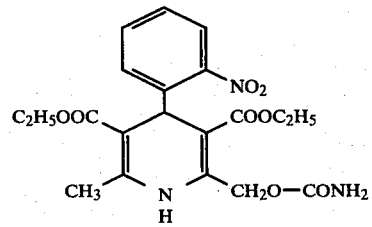

2-Hydroxymethyl-6-methyl-4-(nitrophenyl)-3,5-diethoxycarbonyl-1,4-dihydropyridine (390 mg) was dissolved in benzene (10 ml), chlorosulfonyl isocyanate (0.2 ml) was added thereto, and the mixture was reacted under stirring at room temperature for 30 minutes. Water (10 ml) was added to the reaction mixture under cooling, and the mixture was stirred at room temperature for 30 minutes for hydrolysis. The reaction mixture thereby obtained was extracted with ethyl acetate, and the extracted solution was concentrated under reduced pressure. The residue was recrystallized from ethyl acetate-hexane, whereupon crystals (210 mg, yield: 48.5%) were obtained.

mp.: 128°–132° C.

UV: $\lambda_{max}^{MeOH}$, nm; 235, 350.

IR (KBr), cm⁻¹; 3540, 3400, 3000, 1710, 1690, 1535, 1495, 1340, 1205, 1120, 1100, 1095, 780, 755, 715.

¹H NMR (90 MHz, in CDCl₃), δ in ppm; 1.18 (t, J=7 Hz, 6H), 2.35 (s, 3H), 4.15 (m, 4H), 5.38 (broad s, 4H), 5.96 (s, 1H), 7.1–8.0 (m, 5H).

EXAMPLES 2 TO 6

In a manner similar to Example 1, the compounds listed in Table 3 were obtained.

TABLE 3

| Example No. | Structural formula | Yield % of theory | Melting Point °C. | UV $\lambda_{max}^{MeOH}$, nm |
| --- | --- | --- | --- | --- |

TABLE 3-continued

| Example No. | Structure | Amount / Yield | mp (°C) | λ (nm) |
|---|---|---|---|---|
| 2 | 4-(3-nitrophenyl)-2-methyl-6-(carbamoyloxymethyl)-1,4-dihydropyridine-3,5-dicarboxylic acid dimethyl ester | 150 mg / 34% | 110–114 | 235, 355 |
| 3 | 4-(3-nitrophenyl)-2-methyl-6-(carbamoyloxymethyl)-1,4-dihydropyridine-3,5-dicarboxylic acid diethyl ester | 107 g / 63% | 144–148 | 235, 355 |
| 4 | 4-(3-nitrophenyl)-2-methyl-6-(carbamoyloxymethyl)-1,4-dihydropyridine-3,5-dicarboxylic acid 3-isopropyl 5-ethyl ester | 210 mg / 22% | 130–132 | 235, 355 |
| 5 | 3-(2-chloroethyl) 5-methyl 4-(3-nitrophenyl)-2-methyl-6-(carbamoyloxymethyl)-1,4-dihydropyridine-3,5-dicarboxylate | 6 g / 81% | 166–168 | 236, 355 |
| 6 | 3-(2-chloroethyl) 5-(2-propoxyethyl) 4-(3-nitrophenyl)-2-methyl-6-(carbamoyloxymethyl)-1,4-dihydropyridine-3,5-dicarboxylate | 530 mg / 72% | — | 236, 355 |

| Example No. | IR(KBr): cm$^{-1}$ | $^1$H NMR (90 MHz, CDCl$_3$): δ in ppm |
|---|---|---|
| 2 | 3540, 3360, 2980, 1715, 1690, 1495, 1355, 1340, 1210, 1105, 1090, 830, 805, 790, 755, 710 | 2.38(s,3H), 3.72(s,6H), 5.2(s,1H), 5.35(s,2H), 5.4(s,2H), 7.3–8.25(m,5H) |
| 3 | 3540, 3380, 3000, 1710, 1690, 1490, 1355, 1335, 1210, 1105, 1090, 790, 760, 720 | 1.23(t,J=7Hz,6H), 2.4(s,3H), 4.18(q,J=7Hz,4H), 5.2(s,1H), 5.3(s,2H), 5.4(s,2H), 7.2–8.2(m,5H) |
| 4 | 3450, 3350, 2980, 1705, 1685, 1530, 1485, 1350, 1205, 1100, 1080, 780, 715 | 1.14(t,J=8Hz,3H), 1.27(d,J=6Hz,6H), 1.42(s,3H), 4.15(q,J=8Hz,2H), 5.0(sep,J=6Hz,1H), 5.14(s,1H), 5.3(s,2H), 6.1(m,2H), 7.5–8.4(m,5H) |
| 5 | 3420, 2960, 1740, 1710, 1685, 1645, 1600, 1530, 1475, 1350, 1320, 1205, 1070, 900, 830, 755 | 2.44(s,3H), 3.7(s,3H), 3.7(t,J=6Hz,2H), 4.36(t,J=6Hz,2H), 5.1–5.8(br.s,2H), 5.2(s,1H), 5.33(s,2H), 7.45–8.3(m,5H) |
| 6 | 3500, 3400, 3000, 1710, 1690, 1640, 1600, 1530, 1490, 1350, 1210, 1100, | 0.8,(t,J=7Hz,3H), 1.46(q,J=7Hz,2H) 2.35(s,3H), 3.3(t,J=7Hz,2H), 3.5(t,J=6Hz,2H), 3.75(t,J=5Hz,2H), 4.1(t,J= |

TABLE 3-continued

| | |
|---|---|
| 900, 780, 760, 720 | 6Hz,2H), 4.24(t,J=5Hz,2H), 4.92(d,J=12Hz,1H), 5.05(s,1H), 5.06(d,J=12Hz,1H), 6.6(broad-s,2H), 7.3–8.1(m,4H), 9.0(s,1H) |

EXAMPLE 7

2-N-Methylaminocarbonyloxymethyl-6-methyl-4-(2-nitrophenyl)-3,5-diethoxycarbonyl-1,4-dihydropyridine

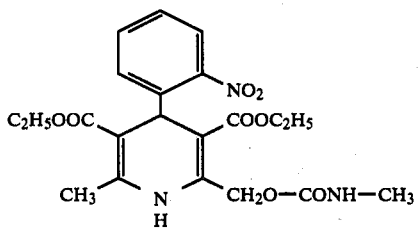

2-Hydroxymethyl-6-methyl-4-(2-nitrophenyl)-3,5-diethoxycarbonyl-1,4-dihydropyridine (220 mg) was dissolved in benzene (10 ml), methyl isocyanate (0.1 ml) and triethylamine (0.3 ml) were added thereto, and the mixture was reacted under reflux for one hour. After cooling the reaction mixture, the crystals precipitated therein were collected by filtration, and recrystallized from di-isopropyl ether/n-hexane, whereupon crystals (140 mg, yield: 56%) were obtained.

mp: 165°–169° C.

UV: $\lambda_{max}^{MeOH}$, nm; 235, 350.

IR (KBr), cm$^{-1}$; 3380, 3000, 1690, 1680, 1535, 1495, 1355, 1280, 1205, 1100, 785, 760, 715.

$^1$H NMR (90 MHz, in CDCl$_3$), $\delta$ in ppm; 1.2 (t, J=7 Hz, 6H), 2.38 (s, 3H), 2.91 (d, J=6 Hz, 3H), 4.18 (m, 4H), 5.15 (m, 1H), 5.38 (s, 2H), 5.98 (s, 1H), 7.2–8.0 (m, 5H)

EXAMPLES 8 TO 17

In a manner similar to Example 7, the compounds listed in Table 4 were obtained.

TABLE 4

| Example No. | Structural formula | Yield % of theory | Melting Point °C | UV MeOH $\lambda_{max}$, nm | IR(KBr): cm$^{-1}$ | $^1$H NMR(90 MHz)*: δ in ppm |
|---|---|---|---|---|---|---|
| 8 | 3-NO$_2$-C$_6$H$_4$ on DHP with COOC$_2$H$_5$, C$_2$H$_5$OOC, CH$_2$O—CONH—CH$_3$, CH$_3$, NH | 260 mg 42% | 192–193 | 235 355 | 3400, 3300, 3000, 1690, 1685, 1480, 1355, 1280, 1205, 1105, 790, 760, 720, | (b); 1.18(t,J=7Hz,6H),2.38(s,3H), 2.67(d,J=5Hz,3H),4.12(q,J=7Hz,4H) 5.13(s,3H),7.22(m,1H),7.5–8.3(m,4H), 9.13(s,1H) |
| 9 | 3-NO$_2$-C$_6$H$_4$ on DHP with COOCH$_3$, CH$_3$OOC, CH$_2$O—CONH—CH$_3$, CH$_3$, NH | 200 mg 39% | 151–153 | 235 355 | 3350, 2950, 1700, 1685, 1530, 1480, 1350, 1275, 1210, 1095, 780, 705 | (a); 2.38(s,3H),2.88(d,J=5Hz,3H), 3.72(s,6H),5.2(s,2H),5.4(s,2H), 7.35–8.3(m,5H) |
| 10 | 3-NO$_2$-C$_6$H$_4$ on DHP with COOC$_2$H$_5$, (CH$_3$)$_2$CHOOC, CH$_2$O—CONH—CH$_3$, CH$_3$, NH | 250 mg 26% | 194–196 | 235 355 | 3380, 3290, 2980, 1680, 1525, 1480, 1350, 1275, 1250, 1205, 1100, 780, 715 | (b); 1.0–1.3(m,9H),2.38(s,3H),2.67 (m,3H),4.1(q,J=7Hz,2H),4.93(sep,J =6Hz,1H),5.1(s,3H),7.2(m,1H), 7.4–8.2(m,4H),9.1(s,1H) |
| 11 | 3-NO$_2$-C$_6$H$_4$ on DHP with COOCH$_3$, Cl—CH$_2$CH$_2$OOC, CH$_2$O—CONH—CH$_3$, CH$_3$, NH | 420 mg 72% | 194–195 | 236 355 | 3400, 3300, 2960, 1690, 1640, 1610, 1530, 1480, 1350, 1280, 1260, 1210, 1110, 905, 830, 780, 760, 715 | (a); 2.47(s,3H),2.85(d,J=5Hz,3H), 3.73(s,3H),3.75(t,J=6Hz,2H), 4.4(t,J=6Hz,2H),5.22(s,1H),5.34 (s,2H),6.7(q,J=5Hz,1H),7.45–8.5 (m,5H) |

TABLE 4-continued

| Example No. | Structural formula | Yield % of theory | Melting Point °C. | UV MeOH $\lambda_{max}$, nm | IR(KBr); cm$^{-1}$ | $^1$H NMR(90 MHz)*: δ in ppm |
|---|---|---|---|---|---|---|
| 12 | [structure: 1,4-dihydropyridine with NO$_2$-phenyl, COOC$_2$H$_5$, CHOOC(CH$_3$)$_2$, CH$_3$, and CH$_2$O—CONH—C$_2$H$_5$ groups] | 370 mg 78% | 153–154.5 | 235 355 | 3350, 2980, 1685, 1530, 1480, 1350, 1275, 1250, 1205, 1095, 780, 715 | (b); 0.9–1.3(m,12H),2.34(s,3H),3.07 (q,J=7Hz,2H),4.07(q,J=8Hz,2H), 4.9(m,1H),5.06(s,3H),7.28(t,J=7Hz, 1H),7.5–8.2(m,4H),9.05(br.s,1H) |
| 13 | [structure: 1,4-dihydropyridine with NO$_2$-phenyl, COOC$_2$H$_5$, CHOOC(CH$_3$)$_2$, CH$_3$, and CH$_2$O—CONH—C$_3$H$_7$ groups] | 440 mg 90% | 150.5–152 | 235 355 | 3350, 2980, 1685, 1530, 1480, 1355, 1270, 1240, 1207, 1100, 780, 715 | (b); 0.88(t,J=8Hz,3H),1.0–1.3(m,9H), 1.48(m,2H),2.38(s,3H),3.04(q,J=7Hz, 2H),4.12(q,J=8Hz,2H),4.14(m,1H), 5.1(s,3H),7.36(t,J=7Hz,1H),7.6– 8.3(m,4H),9.1(s,1H) |
| 14 | [structure: 1,4-dihydropyridine with NO$_2$-phenyl, COOC$_2$H$_5$, CHOOC(CH$_3$)$_2$, CH$_3$, and CH$_2$O—CONH—cyclohexyl groups] | 330 mg 62% | 157–159.5 | 235 355 | 3350, 2940, 1680, 1530, 1480, 1350, 1275, 1207, 1095, 780, 710 | (b); 1.0–1.4(m,9H),1.4–2.0(m,10H), 2.37(s,3H),3.35(br.s,2H),4.1(q,J= 8Hz,2H),4.93(m,1H),5.1(s,3H) |
| 15 | [structure: 1,4-dihydropyridine with NO$_2$-phenyl, COOC$_2$H$_5$, CHOOC(CH$_3$)$_2$, CH$_3$, and CH$_2$O—CONH—phenyl groups] | 370 mg 71% | 134–136 | 238 356 | 3350, 2980, 1685, 1530, 1480, 1350, 1205, 1100, 740, 710, 690 | (b); 1.0–1.4(m,9H),2.4(s,3H),4.12(q,J =8Hz,2H),4.93(m,2H),5.1(s,1H), 5.25(s,2H),7.0–8.3(m,9H),9.27(s,1H), 9.86(s,1H) |

TABLE 4-continued

| Example No. | Structural formula | Yield % of theory | Melting Point °C. | UV MeOH λmax nm | IR(KBr): cm⁻¹ | ¹H NMR(90 MHz)*: δ in ppm |
|---|---|---|---|---|---|---|
| 16 | [Structure: 1,4-dihydropyridine with 3-NO₂-phenyl, COOCH(CH₃)₂, COOC₂H₅, CH₃, and CH₂O—CONH—(4-chlorophenyl) substituents, N—H] | 390 mg 70% | 113–116.5 | 235 355 | 3380, 2980, 1695, 1530, 1350, 1220, 1100, 825, 740, 705 | (b); 0.95–1.35(m,9H),2.37(s,3H), 4.08(q,J=8Hz,2H),4.93(m,1H),5.1(s,1H), 5.36(s,2H),7.3–8.3(m,8H),9.27 (s,1H),10.0(s,1H) |
| 17 | [Structure: 1,4-dihydropyridine with 3-NO₂-phenyl, Cl—CH₂CH₂OOC, COOCH₃, CH₃, and CH₂O—CONH—(4-chlorophenyl) substituents, N—H] | 450 mg 65% | — | 243 355 | 3400, 3000, 1750, 1690, 1670, 1600, 1530, 1480, 1350, 1220, 1100, 900, 805, 750, 700 | — |

*; (a): CDCl₃, (b): DMSO—d₆

EXAMPLE 18

2-Aminocarbonyloxymethyl-6-methyl-4-(3-nitrophenyl)-3-ethoxycarbonyl-5-(β-ethoxyethoxy)carbonyl-1,4-dihydropyridine

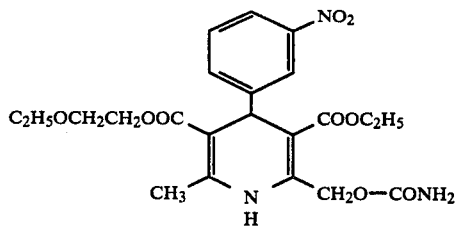

2-Hydroxymethyl-6-methyl-4-(3-nitrophenyl)-3-ethoxycarbonyl-5-(β-ethoxyethoxy)carbonyl-1,4-dihydropyridine (420 mg) was dissolved in benzene (20 ml), chlorosulfonyl isocyanate (0.2 ml) was added thereto, and the mixture was reacted under stirring at room temperature for 30 minutes. Water (10 ml) was added to the reaction mixture under cooling, and the mixture was stirred at room temperature for 30 minutes for hydrolysis. The reaction mixture thus obtained was extracted with ethyl acetate, and the extracted solution was washed with water, dried and then concentrated under reduced pressure. The residue was recrystallized from diisopropyl ether/hexane, whereupon crystals (290 mg, yield: 62.6%) were obtained.

mp: 135°–138° C.

UV: $\lambda_{max}^{MeOH}$, nm; 236, 355.

IR (KBr), cm$^{-1}$; 3520, 3360, 2990, 1705, 1690, 1645, 1610, 1525, 1485, 1350, 1205, 1120, 1105, 1085, 905, 830, 780, 755, 720.

$^1$H NMR (90 MHz, DMSO-d$_6$), δ in ppm; 1.07 (t, J=8 Hz, 3H), 1.15 (t, J=8 Hz, 3H), 2.37 (s, 3H), 3.45 (q, J=8 Hz, 2H), 3.62 (t, J=4 Hz, 2H), 4.08 (q, J=8 Hz, 2H), 4.12 (t, J=4 Hz, 2H), 4.97 (d, J=12 Hz, 1H), 5.1 (s, 1H), 5.13 (d, J=12 Hz, 1H), 6.7 (br, s, 2H), 7.6–8.2 (m, 4H), 9.11 (s, 1H).

EXAMPLES 19 TO 32

In a manner similar to Example 18, the compounds listed in Table 5 were obtained.

TABLE 5

| Example No. | Structural formula | Yield % of theory | Melting Point °C. | UV MeOH $\lambda_{max}$, nm | IR(KBR): cm$^{-1}$ | $^1$H NMR(90 MHz, DMSO—d$_6$): δ in ppm |
|---|---|---|---|---|---|---|
| 19 | (3-NO$_2$-C$_6$H$_4$) dihydropyridine with C$_3$H$_7$OCH$_2$CH$_2$OOC— and —COOC$_2$H$_5$, CH$_3$, CH$_2$O—CONH$_2$ | 350 mg 71% | 147–149 | 236 355 | 3520, 3350, 2950, 1700, 1645, 1610, 1520, 1480, 1350, 1330, 1270, 1200, 1120, 1100, 1080, 905, 830, 780, 755, 720 | 0.85(t,J=8Hz,3H),1.18(t,J=8Hz,3H),1.5(m,2H),2.39(s,3H),3.36(t,J=8Hz,2H),3.57(t,J=5Hz,2H),4.12(q,J=8Hz,2H),4.15(t,J=5Hz,2H),5.0(d,J=13Hz,1H),5.12(s,1H),5.15(d,J=13Hz,1H),6.68(br.s,2H),7.5–8.3(m,4H),9.05(s,1H) |
| 20 | (3-NO$_2$-C$_6$H$_4$) dihydropyridine with i-C$_3$H$_7$OCH$_2$CH$_2$OOC— and —COOC$_2$H$_5$, CH$_3$, CH$_2$O—CONH$_2$ | 310 mg 65% | 139–142 | 235 355 | 3520, 3360, 2980, 1702, 1685, 1645, 1610, 1525, 1485, 1350, 1330, 1270, 1200, 1120, 1080, 900, 825, 780, 755, 720 | 1.06(d,J=6Hz,6H),1.16(t,J=7Hz,3H),2.37(s,3H),3.55(m,1H),3.62(t,J=6Hz,2H),4.09(q,J=7Hz,2H),4.12(t,J=6Hz,2H),4.97(d,J=12Hz,1H),5.1(s,1H),5.13(d,J=12Hz,1H),6.65(br.s,2H),7.5–8.3(m,4H),9.10(s,1H) |
| 21 | (3-NO$_2$-C$_6$H$_4$) dihydropyridine with C$_2$H$_5$OOC— and —COOCH$_2$CH$_2$OCH$_3$, CH$_3$, CH$_2$O—CONH$_2$ | 240 mg 52% | 121–125 | 236 355 | 3480, 3380, 2990, 1690, 1645, 1610, 1530, 1490, 1350, 1275, 1210, 1110, 1095, 1080, 905, 830, 780, 755, 720 | 1.16(t,J=8Hz,3H),2.38(s,3H),3.28(s,3H),3.53(t,J=5Hz,2H),4.08(q,J=8Hz,2H),4.18(t,J=5Hz,2H),5.0(d,J=13Hz,1H),5.11(s,1H),5.13(d,J=13Hz,1H),6.7(br.s,2H),7.5–8.3(m,4H),9.07(s,1H) |
| 22 | (3-NO$_2$-C$_6$H$_4$) dihydropyridine with C$_2$H$_5$OOC— and —COOCH$_2$CH$_2$OC$_3$H$_7$, CH$_3$, CH$_2$O—CONH$_2$ | 430 mg 94% | 136–138.5 | 236 355 | 3500, 3380, 2980, 1710, 1680, 1640, 1600, 1525, 1490, 1350, 1275, 1210, 1095, 905, 830, 780, 760, 715 | 0.83(t,J=7Hz,3H),1.15(t,J=7Hz,3H),1.5(m,2H),2.37(s,3H),3.35(t,J=7Hz,2H),3.56(t,J=3Hz,2H),4.08(q,J=7Hz,2H),4.16(t,J=3Hz,2H),5.0(d,J=13Hz,1H),5.1(s,1H),5.15(d,J=13Hz,1H),6.72(s,2H),7.5–8.3(m,4H),9.07(s,1H) |

TABLE 5-continued

| Example No. | Structural formula | Yield % of theory | Melting Point °C. | UV MeOH $\lambda_{max}$, nm | IR(KBR): cm$^{-1}$ | $^1$H NMR(90 MHz, DMSO-d$_6$): δ in ppm |
|---|---|---|---|---|---|---|
| 23 | CH$_2$=CHCH$_2$OCH$_2$CH$_2$OOC—[dihydropyridine with 3-NO$_2$-phenyl, COOC$_2$H$_5$, CH$_2$O—CONH$_2$, CH$_3$, NH] | 380 mg 78% | 135-139 | 236 355 | 3520, 3360, 2990, 1705, 1685, 1640, 1610, 1520, 1485, 1350, 1330, 1270, 1200, 1120, 1100, 1080, 1000, 920, 900, 825, 780, 755, 720 | 1.16(t,J=8Hz,3H),2.38(s,3H),3.58 (t,J=5Hz,2H),3.98(d,J=9Hz,2H),4.1 (q,J=8Hz,2H),4.15(t,J=5Hz,2H),5.08 (d,J=10Hz,1H),5.1(s,1H),5.1-5.4 (m,2H),5.15(d,J=10Hz,1H),5.6-6.2 (m,1H),6.71(s,2H),7.5-8.3(m,4H), 9.11(s,1H) |
| 24 | [dihydropyridine with 3-NO$_2$-phenyl, COOC$_2$H$_5$, CH$_2$O—CONH$_2$, CH$_3$, NH, OCH$_2$CH$_2$OOC—C$_6$H$_5$] | 405 mg 77% | 89-93 | 235 355 | 3480, 3420, 3360, 2950, 1710, 1690, 1615, 1600, 1530, 1490, 1350, 1335, 1250, 1200, 1125, 1080, 930, 915, 780, 755, 720, 690 | 1.16(t,J=9Hz,3H),2.4(s,3H),3.64 (t,J=7Hz,2H),4.1(q,J=9Hz,2H),4.25 (t,J=7Hz,2H),5.0(d,J=13Hz,1H),5.11 (s,1H),5.16(d,J=13Hz,1H),6.73(br.s, 2H),6.9-7.5(m,5H),7.4-8.3(m,4H), 9.16(s,1H) |
| 25 | C$_6$H$_5$CH$_2$OCH$_2$CH$_2$OOC—[dihydropyridine with 3-NO$_2$-phenyl, COOC$_2$H$_5$, CH$_2$O—CONH$_2$, CH$_3$, NH] | 300 mg 56g | 58.5-62 | 236 355 | 3500, 3360, 2950, 1720, 1700, 1685, 1640, 1610, 1530, 1485, 1350, 1330, 1280, 1210, 1120, 1095, 1085, 905, 830, 780, 740, 700 | 1.15(t,J=7Hz,3H),2.37(s,3H),3.63 (t,J=5Hz,2H),4.1(q,J=7Hz,2H),4.2 (t,J=5Hz,2H),4.52(s,2H),4.98(d,J= 12Hz,1H),5.13(d,J=12Hz,1H),5.13 (s,1H),6.72(s,2H),7.4(s,5H),7.5- 8.3(m,4H),9.11(s,1H) |
| 26 | C$_3$H$_7$OCH$_2$CH$_2$OOC—[dihydropyridine with 3-NO$_2$-phenyl, COOCH$_2$CH$_2$OC$_3$H$_7$, CH$_2$O—CONH$_2$, CH$_3$, NH] | 410 mg 83% | 91-99 | 236 355 | 3510, 3400, 3330, 2960, 2870, 1740, 1695, 1665, 1525, 1475, 1345, 1325, 1275, 1220, 1200, 1120, 1090, 1070, 1015, 905, 830, 785, 755, 710 | 0.82(t,J=7Hz,6H),1.46(m,4H), 2.34(s,3H),3.28(t,J=7Hz,4H),3.5 (t,J=5Hz,4H),4.08(t,J=5Hz,4H), 4.9(d,J=12Hz,1H),5.1(d,J=12Hz,1H), 5.12(s,1H),6.6(s,2H),7.35-8.2 (m,4H),8.95(s,1H) |

TABLE 5-continued

| Example No. | Structural formula | Yield % of theory | Melting Point °C. | UV MeOH $\lambda_{max}$, nm | IR(KBR): cm$^{-1}$ | 1H NMR(90 MHz, DMSO—d$_6$): δ in ppm |
|---|---|---|---|---|---|---|
| 27 | [3-NO$_2$-C$_6$H$_4$ dihydropyridine with COOCH$_2$CH$_2$OCH$_3$, CH$_2$O—CONH$_2$, CH$_3$OCH$_2$CH$_2$OOC, CH$_3$] | 375 mg 76% | 110–115 | 236 355 | 3500, 3400, 3000, 1690, 1640, 1610, 1530, 1485, 1350, 1330, 1280, 1210, 1110, 1095, 905, 830, 780, 755, 720 | 2.38(s,3H),3.3(s,6H),3.53(t,J=5Hz,4H),4.12(t,J=5Hz,4H),5.05(d,J=13Hz,1H),5.1(s,1H),5.15(d,J=13Hz,1H),6.7(s,2H),7.5–8.3(m,4H),9.1(s,1H) |
| 28 | [2-NO$_2$-C$_6$H$_4$ dihydropyridine with COOC$_2$H$_5$, CH$_2$O—CONH$_2$, C$_3$H$_7$OCH$_2$CH$_2$OOC, CH$_3$] | 320 mg 65% | 120–126 | 234 340 | 3400, 2970, 1710, 1690, 1640, 1605, 1530, 1490, 1335, 1320, 1280, 1205, 1110, 1100, 1080, 860, 830, 780, 755, 710 | 0.78(t,J=7Hz,3H),1.08(t,J=8Hz,3H),1.4(m,2H),2.28(s,3H),3.23(t,J=7Hz,2H),3.47(t,J=8Hz,2H),4.02(q,J=8Hz,2H),4.05(t,J=8Hz,2H),4.83(d,J=13Hz,1H),5.0(d,J=13Hz,1H),5.63(s,1H),6.6(br.s,2H),7.2–7.9(m,4H),8.86(s,1H) |
| 29 | [4-NO$_2$-C$_6$H$_4$ dihydropyridine with COOC$_2$H$_5$, CH$_2$O—CONH$_2$, C$_3$H$_7$OCH$_2$CH$_2$OOC, CH$_3$] | 230 mg 47% | 117–121 | 233 280 370 | 3500, 3400, 3000, 1690, 1640, 1610, 1530, 1485, 1350, 1330, 1280, 1210, 1110, 1095, 905, 830, 780, 755, 720 | 0.85(t,J=8Hz,3H),1.15(t,J=8Hz,3H),1.5(m,2H),2.38(s,3H),3.36(t,J=8Hz,2H),3.55(t,J=4Hz,2H),4.03(q,J=8Hz,2H),4.15(t,J=4Hz,2H),4.9(d,J=8Hz,2H),5.02(s,1H),5.05(d,J=12Hz,1H),6.6(s,2H),7.42(d,J=9Hz,2H),8.1(d,J=9Hz,2H),8.94(s,1H) |
| 30 | [2-CN-C$_6$H$_4$ dihydropyridine with COOCH$_2$CH$_2$OCH$_3$, CH$_2$O—CONH$_2$, CH$_3$OCH$_2$CH$_2$OOC, CH$_3$] | 540 mg 65% | 162–166 | 235 365 | 3540, 3380, 3000, 2230, 1710, 1690, 1640, 1605, 1490, 1390, 1335, 1275, 1200, 1120, 1090, 1040, 940, 840, 775 | 2.36(s,3H),3.28(s,6H),3.53(t,J=4Hz,4H),4.18(t,J=4Hz,4H),4.97(d,J=13Hz,1H),5.13(d,J=13Hz,1H),5.25(s,1H),6.73(br.s,2H),7.3–7.9(m,5H),8.97(s,1H) |

TABLE 5-continued
| Example No. | Structural formula | Yield % of theory | Melting Point °C. | UV MeOH $\lambda_{max}$, nm | IR(KBR): cm$^{-1}$ | $^1$H NMR(90 MHz, DMSO—$d_6$): δ in ppm |
|---|---|---|---|---|---|---|
| 31 | 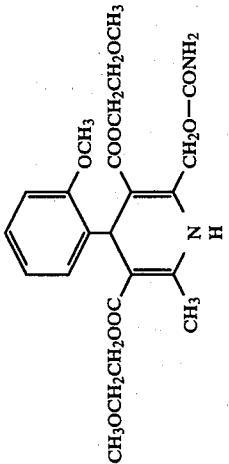 | 440 mg 52% | — | 235 355 | 3420, 3350, 2980, 1720, 1680, 1605, 1490, 1380, 1320, 1280, 1210, 1110, 1095, 860, 750 | 2.26(s,3H),3.27(s,6H),3.5(t,J=4Hz,4H),3.7(s,3H),4.08(t,J=4Hz,4H),4.88(d,J=12Hz,1H),5.02(d,J=12Hz,1H),5.2(s,1H),6.58(s,2H),6.7–7.3(m,5H),8.57(s,1H) |
| 32 | 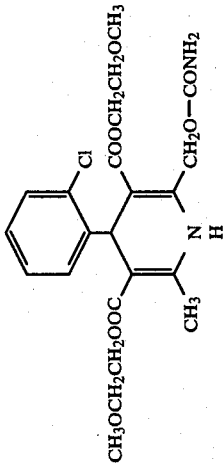 | 540 mg 72% | 122–128 | 237 357 | 3420, 2980, 1705, 1685, 1640, 1605, 1490, 1385, 1370, 1330, 1280, 1205, 1110, 1100, 1080, 1040, 830, 755 | 2.31(s,3H),3.28(s,6H),3.52(t,J=4Hz,4H),4.13(t,J=4Hz,4H),4.9(d,J=13Hz,1H),5.1(d,J=13Hz,1H),5.38(s,1H),6.7(br.s,2H),7.1–7.6(m,5H),8.85(s,1H) |

EXAMPLE 33

2-N-Methylaminocarbonyloxymethyl-6-methyl-4-(3-nitrophenyl)-3-ethoxycarbonyl-5-(β-ethoxyethoxy)carbonyl-1,4-dihydropyridine

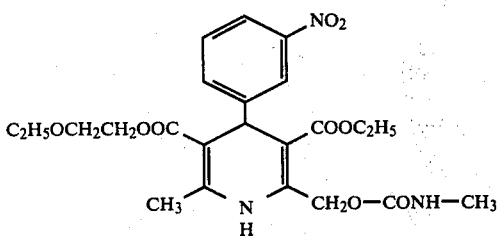

2-Hydroxymethyl-6-methyl-4-(3-nitrophenyl)-3-ethoxycarbonyl-5-(β-ethoxyethoxy)carbonyl-1,4-dihydropyridine (420 mg) was dissolved in benzene (20 ml), methyl isocyanate (0.1 ml) and triethylamine (0.3 ml) were added thereto, and the mixture was reacted under reflux for one hour. After cooling the reaction mixture, it was extracted with ethyl acetate, and the extracted solution was washed with water, dried and then concentrated under reduced pressure. The residue was recrystallized from diisopropyl ether/hexane, whereupon crystals (200 mg, yield: 42%) were obtained.

mp: 148°–149° C.

UV: $\lambda_{max}^{MeOH}$, nm; 236, 355.

IR (KBr), cm$^{-1}$; 3390, 3280, 2980, 1680, 1640, 1610, 1535, 1480, 1355, 1280, 1205, 1120, 1095, 905, 830, 780, 760, 715.

$^1$H NMR (90 MHz, DMSO-d$_6$), δ in ppm; 1.11 (t, J=8 Hz, 3H), 1.19 (t, J=7 Hz, 3H), 2.39 (s, 3H), 2.67 (d, J=4.5 Hz, 3H), 3.48 (q, J=8 Hz, 2H), 3.65 (t, J=5 Hz, 2H), 4.12 (q, J=7 Hz, 2H), 4.15 (t, J=5 Hz, 2H), 5.06 (d, J=12 Hz, 1H), 5.14(s, 1H), 5.18 (d, J=12 Hz, 1H), 7.22 (m, 1H), 7.6–8.25 (m, 4H), 9.18 (s, 1H)

EXAMPLES 34 TO 42

In a manner similar to Example 33, the compounds listed in Table 6 were obtained.

TABLE 6

| Example No. | Structural formula | Yield % of theory | Melting Point °C. | UV $\lambda_{max}^{MeOH}$, nm |
|---|---|---|---|---|
| 34 | (C$_3$H$_7$OCH$_2$CH$_2$OOC / COOC$_2$H$_5$ / CH$_3$ / CH$_2$O—CONH—CH$_3$; 3-NO$_2$-phenyl) | 340 mg 67% | 136–137 | 236 355 |
| 35 | (i-C$_3$H$_7$OCH$_2$CH$_2$OOC / COOC$_2$H$_5$ / CH$_3$ / CH$_2$O—CONH—CH$_3$; 3-NO$_2$-phenyl) | 420 mg 85% | 120–122 | 235 355 |
| 36 | (C$_2$H$_5$OOC / COOCH$_2$CH$_2$OCH$_3$ / CH$_3$ / CH$_2$O—CONH—CH$_3$; 3-NO$_2$-phenyl) | 290 mg 60% | 152–156 | 235 355 |
| 37 | (C$_2$H$_5$OOC / COOCH$_2$CH$_2$OC$_3$H$_7$ / CH$_3$ / CH$_2$O—CONH—CH$_3$; 3-NO$_2$-phenyl) | 360 mg 71% | 152–155.5 | 236 355 |

TABLE 6-continued

| 38 | [Structure: 1,4-dihydropyridine with 3-nitrophenyl at C4; C3H7OCH2CH2OOC and COOCH2CH2OC3H7 ester groups at C3 and C5; CH3 at C6; CH2O—CONH—CH3 at C2; NH in ring] | 330 mg 65% | 119–120 | 236 355 |

| Example No. | IR(KBr): cm$^{-1}$ | $^1$H NMR (90 MHz, DMSO—d$_6$): δ in ppm |
|---|---|---|
| 34 | 3380, 3290, 2970, 1680, 1640, 1610, 1530, 1480, 1350, 1275, 1200, 1120, 1100, 905, 830, 780, 760, 715 | 0.82,(t,J=8Hz,3H), 1.13(t,J=8Hz, 3H), 1.48(m,2H), 2.35(s,3H), 2.63 (d,J=6Hz,3H), 3.33(t,J=8Hz,2H), 3.54(t,J=5Hz,2H), 4.07(q,J=8Hz, 2H), 4.11(t,J=5Hz,2H), 5.0(d,J=13Hz, 1H), 5.09(s,1H), 5.13(d,J=13Hz,1H), 7.15(m,1H), 7.5–8.3(m,4H), 9.10 (s,1H) |
| 35 | 3370, 2980, 1680, 1640, 1610, 1530, 1480, 1350, 1275, 1205, 1120, 1095, 905, 830, 780, 760, 710 | 1.06(d,J=7Hz,6H), 1.16(t,J=8Hz, 3H), 2.37(s,3H), 2.65(d,J=6Hz,3H), 3.56(m,1H), 3.60(t,J=7Hz,2H), 4.09(q,J= 8Hz,2H), 4.10(t,J=7Hz,2H), 5.03(d,J= 13Hz,1H), 5.11(s,1H), 5.14(d,J=13Hz, 1H), 7.16(m,1H), 7.5–8.3(m,4H), 9.12 (s,1H) |
| 36 | 3370, 3280, 2980, 1680, 1640, 1610, 1530, 1480, 1350, 1275, 1205, 1100, 905, 830, 780, 760, 715 | 1.17(t,J=7Hz,3H), 2.37(s,3H), 2.65(d,J=5Hz,3H), 3.27(s,3H), 3.52 (t,J=5Hz,2H), 4.10(q,J=7Hz,2H), 4.16(t,J=5Hz,2H), 5.06(d,J=14Hz,1H), 5.1(s,1H), 5.14(t,J=14Hz,1H), 7.18 (m,1H), 7.5–8.3(m,4H), 9.12(s,1H) |
| 37 | 3380, 2980, 1680, 1640, 1610, 1530, 1485, 1355, 1280, 1205, 1100, 910, 830, 780, 760, 715 | 0.86,(t,J=7Hz,3H), 1.2(t,J=7Hz, 3H), 1.52(m,2H), 2.4(s,3H), 2.68(d,J= 6Hz,3H), 3.38(t,J=7Hz,2H), 3.58 (t,J=4Hz,2H), 4.1(q,J=7Hz,2H), 4.18(t,J=4Hz,2H), 5.09(d,J=13Hz,1H), 5.13(s,1H), 5.18(d,J=13Hz,1H), 7.2 (m,1H), 7.4–8.4(m,4H), 9.12(s,1H) |
| 38 | 3350, 3300, 2960, 2870, 1685, 1635, 1600, 1530, 1480, 1350, 1275, 1250, 1200, 1130, 1100, 1015, 990, 900, 830, 780, 760, 750, 710 | 0.83(t,J=7Hz,6H), 1.5(m,4H), 2.35(s,3H), 2.62(d,J=5Hz,3H), 3.3 (t,J=7Hz,4H), 3.52(t,J=4Hz,4H), 4.12 (t,J=4Hz,4H), 5.0(d,J=13Hz,1H), 5.1 (d,J=13Hz,1H), 5.14(s,1H), 7.1(m,1H), 7.4–8.3(m,4H), 9.0(s,1H) |

| Example No. | Structural formula | Yield % of theory | Melting Point °C. | UV $\lambda_{max}^{MeOH}$, nm |
|---|---|---|---|---|
| 39 | [Structure: 1,4-dihydropyridine with 3-nitrophenyl at C4; C2H5OOC and COOCH2CH2OCH3 esters; CH3 at C6; CH2O—CONH—cyclohexyl at C2; NH in ring] | 330 mg 61% | 148–152 | 235 355 |
| 40 | [Structure: 1,4-dihydropyridine with 3-nitrophenyl at C4; C2H5OCH2CH2OOC and COOC2H5 esters; CH3 at C6; CH2O—CONH—phenyl at C2; NH in ring] | 370 mg 69% | 138–142 | 238 356 |

TABLE 6-continued

41

$C_3H_7OCH_2CH_2OOC$, $COOCH_2CH_2OC_3H_7$, 4-(3-nitrophenyl), $CH_3$, N-H, $CH_2O$—CONH—(4-Cl-phenyl)

420 mg  140–145  242
67%               357

42

$C_3H_7OCH_2CH_2OOC$, $COOCH_2CH_2OC_3H_7$, 4-(3-nitrophenyl), $CH_3$, N-H, $CH_2O$—CONH—(3,4-diCl-phenyl)

395 mg  128–135  243
60%               355

| Example No. | IR(KBr): cm$^{-1}$ | $^1$H NMR (90 MHz, DMSO—d$_6$): δ in ppm |
|---|---|---|
| 39 | 3350, 2950, 1680, 1640, 1610, 1530, 1480, 1350, 1310, 1210, 1095, 1060, 900, 830, 780, 740, 710 | 1.18(t,J=8Hz,3H), 1.7(br.s,10H), 2.37(s,3H), 3.25(s,3H), 3.35(m,1H), 3.5(t,J=4Hz,2H), 4.08(q,J=8Hz,2H), 4.15(t,J=4Hz,2H), 5.05(d,J=13Hz,1H), 5.1(s,1H), 5.15(d,J=13Hz,1H), 7.25(d,J=7Hz,1H), 7.5–8.3(m,4H), 9.1(s,1H) |
| 40 | 3350, 3000, 1685, 1645, 1600, 1530, 1480, 1350, 1310, 1205, 1100, 1080, 1070, 905, 850, 825, 770, 740, 710, 690 | 1.1(t,J=7Hz,3H), 1.2(t,J=7Hz,3H), 2.4(s,3H), 3.5(q,J=7Hz,2H), 3.65(t,J=5Hz,2H), 4.1(q,J=7Hz,2H), 4.15(t,J=5Hz,2H), 5.05(d,J=12Hz,1H), 5.15(s,1H), 5.2,(d,J=12Hz,1H), 7.0–8.3(m,9H), 9.27(s,1H), 9.86(s,1H) |
| 41 | 3400, 3000, 1700, 1600, 1530, 1490, 1480, 1350, 1280, 1220, 1100, 1070, 1030, 900, 825, 770, 740, 705 | 0.85(t,J=7Hz,6H), 1.5(m,4H), 2.4 (s,3H), 3.37(t,J=7Hz,4H), 3.6(t,J=4Hz, 4H), 4.18(t,J=4Hz,4H), 5.15(s,1H), 5.15 (d,J=12Hz,1H), 5.34(d,J=12Hz,1H), 7.43 (d,J=9Hz,2H), 7.63(d,J=9Hz,2H), 7.5– 8.3(m,5H), 9.15(s,1H) |
| 42 | 3420, 3300, 3100, 3000, 1750, 1690, 1670, 1610, 1595, 1530, 1480, 1350, 1290, 1220, 1120, 1100, 910, 810, 755, 710 | 0.85(t,J=7Hz,6H), 1.5(m,4H), 2.4 (s,3H), 3.38(t,J=7Hz,4H), 3.58(t,J= 4Hz,4H), 4.18(t,J=4Hz,4H), 5.04 (s,1H), 5.05(d,J=12Hz,1H), 5.25(d,J= 12Hz,1H), 7.3–8.2(m,8H), 9.2(s,1H) |

EXAMPLE 43

2-Aminocarbonyloxymethyl-6-methyl-4-(3-nitrophenyl)-3-methoxycarbonyl-5-(β-N-methylbenzylaminoethoxy)carbonyl-1,4-dihydropyridine

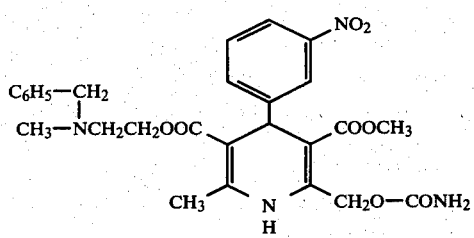

2-Aminocarbonyloxymethyl-6-methyl-4-(3-nitrophenyl)-3-methoxycarbonyl-5-β-chloroethoxycarbonyl-1,4-dihydropyridine (5.8 g) was dissolved in propanol (50 ml), N-methylbenzylamine (8 ml) and sodium iodide (0.2 g) were added, and the mixture was reacted under reflux and heating for 8 hours. The reaction mixture was concentrated, and the residue was extracted with ethyl acetate (100 ml). The extracted solution was washed sequentially with 0.5 N hydrochloric acid, a sodium hydrogen carbonate solution and water, and then concentrated under reduced pressure, whereupon an oily residue was obtained. This residue was separated and purified by silica gel column chromatography with use of ethyl acetate as the developer solvent. HCl-ethanol was added to the acetone solution and the precipitates thereby formed were collected and recrystallized from acetone/ethyl acetate, whereupon crystals (3.8 g, yield; 53.5%) were obtained.

mp; 117.5°–121° C.

UV: $\lambda_{max}^{MeOH}$, nm; 236, 355.

IR (KBr), cm$^{-1}$; 3400, 2950, 1720, 1690, 1640, 1610, 1525, 1475, 1350, 1320, 1210, 1010, 900, 825, 780, 740, 700.

$^1$H NMR (90 MHz, DMSO-d$_6$), δ in ppm; 2.37 (s, 3H), 2.57 (s, 3H), 3.36 (m, 2H), 3.68 (s, 3H), 4.25 (s, 2H), 4.43 (m, 2H), 4.88 (d, J-14 Hz, 1H), 5.03 (d, J=14 Hz, 1H), 5.03 (s, 1H), 6.73 (br, s, 2H), 7.42 (s, 5H), 7.5–8.2 (m, 4H), 9.2 (s, 1H).

EXAMPLES 44 TO 50

In a manner similar to Example 43, the compounds listed in Table 7 were obtained.

TABLE 7

| Example No. | Structural formula | Yield % of theory | Melting Point °C. | UV $\lambda_{max}^{MeOH}$, nm |
|---|---|---|---|---|
| 44 | [3-nitrophenyl dihydropyridine with C₆H₅CH₂, CH₃—NCH₂CH₂OOC / COOCH₃ / CH₃ / CH₂O—CONH—CH₃ · HCl] | 210 mg 50% | 77–82 | 236 353 |
| 45 | [same backbone with CH₂O—CONH—C₆H₄—Cl (4-Cl) · HCl] | 200 mg 44% | — | 236 353 |
| 46 | [piperidino-NCH₂CH₂OOC / COOCH₃ / CH₂O—CONH₂ · HCl] | 300 mg 50% | 75–80 | 228 342 |
| 47 | [4-methylpiperazinyl-NCH₂CH₂OOC / COOCH₃ / CH₂O—CONH₂ · 2HCl] | 310 mg 46% | 163–168 | 231 345 |
| 48 | [morpholino-NCH₂CH₂OOC / COOCH₃ / CH₂O—CONH₂ · HCl] | 350 mg 63% | 68–75 | 235 355 |

| Example No. | IR(KBr): cm$^{-1}$ | $^1$H NMR (90 MHz, DMSO—d$_6$): δ in ppm |
|---|---|---|
| 44 | 3380, 3330, 2960, 1690, 1640, 1605, 1530, 1480, 1350, 1280, 1250, 1210, 1105, 1050, 905, 830, 780, 740, 700 | 2.13(s,3H), 2.36(s,3H), 2.6(t,J= 6Hz,2H), 2.65(d,J=5Hz,3H), 3.5(s,2H), 3.62(s,3H), 4.16(t,J=6Hz,2H), 5.1(d,J=13Hz,1H), 5.13(s,1H), 5.16 (d,J=13Hz,1H), 7.2(m,1H), 7.33(s,5H), 7.4–8.3(m,4H), 9.16(s,1H) |
| 45 | 3400, 3320, 2960, 1740 1690, 1640, 1605, 1530, 1480, 1350, 1280, 1250, 1210, 1100, 905, 830, 780, 750, 720 | 2.13(s,3H), 2.36(s,3H), 2.6(t,J= 6Hz,2H), 3.5(s,2H), 3.62(s,3H), 4.16(t,J=6Hz,2H), 5.13(s,1H), 5.13 (d,J=12Hz,1H), 5.33(d,J=12Hz,1H), 7.3–8.3(m,9H), 7.33(s,5H), 9.2(s,1H) |
| 46 | 3400, 2950, 1740, 1685, 1525, 1500, 1350, 1245, 1200, 1190, 1090, 1020, 1010, 975, 900, 825, | 1.7(br.s,6H), 2.46(s,3H), 2.8 (br.s,4H), 3.3(s,3H), 3.3(m,2H), 4.35 (m,2H), 4.9(s,2H), 5.05(s,1H), 5.25(br.s,2H), 7.5–8.3(m,4H), |

TABLE 7-continued

| | IR(KBr): cm⁻¹ | ¹H NMR (90 Hz, DMSO—d₆): δ in ppm |
|---|---|---|
| | 800, 760, 730, 690 | 9.35(s,1H) |
| 47 | 3420, 1690, 1525, 1500, 1350, 1210, 1095, 1010, 975, 900, 830, 800, 780, 760, 740 | 2.48(s,3H), 2.9(s,3H), 3.3–4.0 (br.s,10H), 3.7(s,3H), 4.5(m,2H), 5.02(d,J=12Hz,1H), 5.15(s,1H), 5.2 (d,J=12Hz,1H), 6.8(br.s,2H), 7.6–8.3 (m,4H), 9.38(s,1H) |
| 48 | 3450, 2960, 1690, 1640, 1610, 1530, 1480, 1350, 1330, 1280, 1210, 1100, 1070, 1020, 910, 830, 780, 760, 710 | 2.45,(s,3H), 2.9–4.1(m,10H), 3.68(s,3H), 4.5(m,2H), 4.97(d,J= 13Hz,1H), 5.12(s,1H), 5.14(d,J= 13Hz,1H), 6.73(br.s,2H), 7.5–8.3 (m,4H), 9.35(s,1H) |

| Example No. | Structural formula | Yield % of theory | Melting Point °C. | UV $\lambda_{max}^{MeOH}$, nm |
|---|---|---|---|---|
| 49 | [structure: 1,4-dihydropyridine with 3-nitrophenyl, NCH₂CH₂OOC with N(C₂H₅)₂, COOCH₃, CH₃, CH₂O—CONH₂, .HCl] | 340 mg 63% | — | 230 345 |
| 50 | [structure: 1,4-dihydropyridine with 3-nitrophenyl, CH₃—N(C₆H₅CH₂)CH₂CH₂OOC, COOCH₂CH₂OC₃H₇, CH₃, CH₂O—CONH₂, .HCl] | 200 mg 41% | 71–72 | 235 355 |

| Example No. | IR(KBr): cm⁻¹ | ¹H NMR (90 Hz, DMSO—d₆): δ in ppm |
|---|---|---|
| 49 | 3420, 2950, 1735, 1685, 1525, 1500, 1350, 1240, 1200, 1190, 1090, 1020, 975, 900, 825, 800, 760, 730, 690 | 1.19(m,6H), 2.45(s,3H), 3.06(m,4H), 3.25(t,J=7Hz,2H), 3.55(s,3H), 4.36 (t,J=7Hz,2H), 4.93(s,2H), 5.08(s,1H), 6.75(br.s,2H), 7.5–8.3(m,4H), 9.4(br.s,1H) |
| 50 | 3420, 2960, 1690, 1640, 1610, 1530, 1480, 1350, 1320, 1280, 1210, 1080, 900, 830, 810, 780, 740, 700 | 0.8(t,J=8Hz,3H), 1.46(m,2H), 2.4(s,3H), 2.6(s,3H), 3.48(t,J=8Hz,2H), 3.52(m,2H), 3.68(m,2H), 4.12(m,2H), 4.26(br.s,2H), 4.44(m,2H), 4.88 (d,J=13Hz,1H), 5.03(s,1H), 5.08 (d,J=13Hz,1H), 6.65(br.s,2H), 7.43(s,5H), 7.5–8.2(m,4H), 9.2(s,1H) |

EXAMPLE 51

2-N-Cyclohexylaminocarbonyloxymethyl-6-methyl-4-(3-nitrophenyl)-3-ethoxycarbonyl-5-isopropoxycarbonyl-1,4-dihydropyridine 2-Hydroxymethyl-6-methyl-4-(3-nitrophenyl)-3-ethoxycarbonyl-5-isopropoxycarbonyl-1,4-dihydropyridine (404 mg), S-methyl-N-cyclohexylthiolcarbamate (600 mg) and triethylamine (0.4 ml) were added to a mixed solution of pyridine (10 ml) and acetonitrile (2 ml) and the mixture was mixed. While cooling and stirring the mixture, silver nitrate (220 mg) was dropwise added thereto. The mixture thereby obtained was reacted under heating at 100° C. for 4 hours. After cooling the reaction mixture, ethylacetate was added thereto, and after removing the precipitates by filtration, the filtrate was washed with water and dried. The solvent was distilled off by concentration under reduced pressure. The residue was recrystallized from diisopropyl ether/hexane, whereupon crystals (250 mg, yield: 47.2%) were obtained.

The substance thus obtained had a melting point of 157° to 159° C., and the analytical data obtained by UV, IR and ¹H NMR were found to correspond to the product of Example 14.

We claim:

1. A 2-substituted or unsubstituted aminocarbonyloxyalkyl-1,4-dihydropyridine represented by the formula

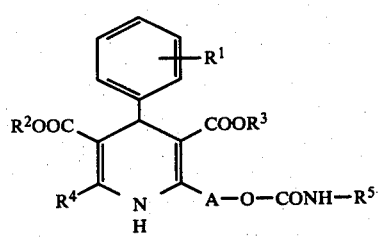

(I)

where R¹ is halogen, nitro, cyano or lower alkoxy; each of R² and R³ is lower alkyl, lower haloalkyl, lower alkoxyalkyl, aralkyloxyalkyl, aryloxyalkyl, lower alkenoxyalkyl, N,N-di-lower alkylaminoalkyl, N-lower alkyl-N-aralkylaminoalkyl, piperidylalkyl, 4-lower alkyl piperazinylalkyl, morpholinoalkyl or 1-pyrrolidinylalkyl; $R^4$ is lower alkyl; A is lower alkylene; and $R^5$ is hydrogen, lower alkyl, cycloalkyl of 3 to 7 carbon atoms, or carbocyclic aryl or pyridyl unsubstituted or substituted by one or two substituents selected from halogen, nitro, lower alkyl, lower alkoxy, di-lower alkylamino and cyano.

2. The compound according to claim 1 wherein $R^1$ is chlorine, bromine, iodine, nitro, cyano, methoxy, ethoxy, propoxy or butoxy, each of $R^2$ and $R^3$ is methyl, ethyl, propyl, isopropyl, butyl, isobutyl, tert.-butyl, pentyl, hexyl, β-chloroethyl, β-bromoethyl, β-chloropropyl, γ-chloropropyl, β,β-dichloroethyl, β,β,β-trichloroethyl, β-methoxyethyl, β-ethoxyethyl, β-propoxyethyl, β-isopropoxyethyl, β-butoxyethyl, β-isobutoxyethyl, γ-tert.-butoxyethyl, β-methoxypropyl, β-ethoxypropyl, β-propoxypropyl, γ-methoxypropyl, γ-ethoxypropyl, γ-propoxypropyl, β-benzyloxyethyl, β-phenethyloxyethyl, β-(p-bromobenzyloxy)ethyl, β-phenoxyethyl, β-(p-chlorophenoxy)ethyl, β-tolyloxyethyl, β-vinyloxyethyl, β-allyloxyethyl, β-(3-butenyloxy)ethyl, β-dimethylaminoethyl, β-diethylaminoethyl, β-ethylmethylaminoethyl, β-benzylmethylaminoethyl, β-benzylethylaminoethyl, β-(p-bromobenzylmethylamino)ethyl, β-(α-methylbenzylmethylamino)ethyl, β-piperidylethyl, β-piperidylpropyl, β-(4-methylpiperazinyl)ethyl, β-(4-ethylpiperazinyl)ethyl, β-(4-methylpiperazinyl)propyl, β-morpholinoethyl, β-morpholinopropyl or γ-morpholinopropyl, $R^4$ is methyl, ethyl, propyl or isopropyl, A is ethylene or propylene which may be unsubstituted or substituted by methyl, ethyl or isopropyl, and $R^5$ is hydrogen, methyl, ethyl, propyl, isopropyl, butyl, isobutyl, tert.-butyl, pentyl, hexyl, cyclopropyl, cyclobutyl, cyclopentyl, cyclohexyl, cycloheptyl, phenyl, p-chlorophenyl, p-bromophenyl, p-fluorophenyl, m,p-dichlorophenyl, p-nitrophenyl, p-tolyl, p-methoxyphenyl, p-dimethylaminophenyl, p-cyanophenyl, α-pyridyl, β-pyridyl, or γ-pyridyl.

3. The compound according to claim 1 which is 2-aminocarbonyloxymethyl-6-methyl-4-(2-nitrophenyl)-3,5-diethoxycarbonyl-1,4-dihydropyridine, 2-N-methylaminocarbonyloxymethyl-6-methyl-4-(2-nitrophenyl)-3,5-diethoxycarbonyl-1,4-dihydropyridine, 2-aminocarbonyloxymethyl-6-methyl-4-(3-nitrophenyl)-3-ethoxycarbonyl-5-isopropoxycarbonyl-1,4-dihydropyridine, 2-N-methylaminocarbonyloxymethyl-6-methyl-4-(3-nitrophenyl)-3-ethoxycarbonyl-5-isopropoxycarbonyl-1,4-dihydropyridine, 2-N-phenylaminocarbonyloxymethyl-6-methyl-4-(3-nitrophenyl)-3-ethoxycarbonyl-5-isopropoxycarbonyl-1,4-dihydropyridine, 2-N-methylaminocarbonyloxymethyl-6-methyl-4-(3-nitrophenyl)-3-methoxycarbonyl-5-(β-N-methylbenzylaminoethoxy)carbonyl-1,4-dihydropyridine, 2-N-methylaminocarbonyloxymethyl-6-methyl-4-(3-nitrophenyl)-3,5-diethoxycarbonyl-1,4-dihydropyridine, 2-N-methylaminocarbonyloxymethyl-6-methyl-4-(3-nitrophenyl)-3,5-dimethoxycarbonyl-1,4-dihydropyridine, 2-aminocarbonyloxymethyl-6-methyl-4-(3-nitrophenyl)-3-ethoxycarbonyl-5-(β-propoxyethoxy)carbonyl-1,4-dihydropyridine, 2-aminocarbonyloxymethyl-6-methyl-4-(3-nitrophenyl)-5-ethoxycarbonyl-3-(β-propoxyethoxy)carbonyl-1,4-dihydropyridine, 2-aminocarbonyloxymethyl-6-methyl-4-(2-nitrophenyl)-3-ethoxycarbonyl-5-(β-propoxyethoxy)carbonyl-1,4-dihydropyridine, 2-aminocarbonyloxymethyl-6-methyl-4-(3-nitrophenyl)-3-methoxycarbonyl-5-β-(4-methyl-1-piperazinyl)ethoxycarbonyl-1,4-dihydropyridine or 2-aminocarbonyloxymethyl-6-methyl-4-(3-nitrophenyl)-3-methoxycarbonyl-5-(β-morpholinoethoxy)carbonyl-1,4-dihydropyridine.

4. The compound according to claim 1 which is 2-aminocarbonyloxymethyl-6-methyl-4-(3-nitrophenyl)-3,5-dimethoxycarbonyl-1,4-dihydropyridine.

5. The compound according to claim 1 which is 2-aminocarbonyloxymethyl-6-methyl-4-(3-nitrophenyl)-3,5-diethoxycarbonyl-1,4-dihydropyridine.

6. The compound according to claim 1 which is 2-aminocarbonyloxymethyl-6-methyl-4-(3-nitrophenyl)-3,5-bis[(β-propoxyethoxy)carbonyl]-1,4-dihydropyridine.

7. The compound according to claim 1 which is 2-N-methylaminocarbonyloxymethyl-6-methyl-4-(3-nitrophenyl)-3,5-bis[(β-propoxyethoxy)carbonyl]-1,4-dihydropyridine.

8. The compound according to claim 1 which is 2-aminocarbonyloxymethyl-6-methyl-4-(3-nitrophenyl)-3-(β-propoxyethoxy)carbonyl-5-(β-N-methylbenzylaminoethoxy)carbonyl-1,4-dihydropyridine.

9. The compound according to claim 1 which is 2-(4-chlorophenyl)aminocarbonyloxymethyl-6-methyl-4-(3-nitrophenyl)-3-ethoxycarbonyl-5-isopropoxycarbonyl-1,4-dihydropyridine.

* * * * *